United States Patent
Beard

(10) Patent No.: US 7,930,128 B2
(45) Date of Patent: Apr. 19, 2011

(54) ROBUST DAMAGE DETECTION

(75) Inventor: Shawn J. Beard, Livermore, CA (US)

(73) Assignee: Acellent Technologies, Inc., Sunnyvale, CA (US)

( * ) Notice: Subject to any disclaimer, the term of this patent is extended or adjusted under 35 U.S.C. 154(b) by 332 days.

(21) Appl. No.: 11/952,944

(22) Filed: Dec. 7, 2007

(65) Prior Publication Data

US 2008/0255771 A1    Oct. 16, 2008

Related U.S. Application Data

(60) Provisional application No. 60/912,112, filed on Apr. 16, 2007.

(51) Int. Cl.
*G01R 31/00* (2006.01)
(52) U.S. Cl. ............ 702/117; 702/34; 702/36; 702/105
(58) Field of Classification Search .................. 702/34, 702/35, 36, 76, 109, 116, 181, 117; 73/579, 73/802
See application file for complete search history.

(56) References Cited

U.S. PATENT DOCUMENTS 6,006,163 A * 12/1999 Lichtenwalner et al. ........ 702/36
7,366,627 B2 * 4/2008 Gordon et al. ................ 702/105
2008/0255775 A1 * 10/2008 Beard et al. .................... 702/35

* cited by examiner

*Primary Examiner* — John H Le
(74) *Attorney, Agent, or Firm* — Innovation Counsel LLP

(57) ABSTRACT

A method of improving damage detection in a structural health monitoring system includes obtaining a baseline set of signals corresponding to a range of values of an environmental effect variable for a plurality of first selected paths between pairs of a plurality of transducers configured in an array attached to a structure. Threshold levels are established for each of the selected paths for determining detection of damage in the structure based on differences in the baseline set of signals for the selected path. A current signal is acquired for each of the selected paths. The plurality of current signals are analyzed based on the threshold levels to detect damage in the structure.

26 Claims, 8 Drawing Sheets

*Fig. 7*
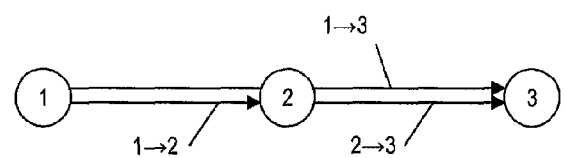
*Fig. 8A*  *Fig. 8B*  *Fig. 8C*
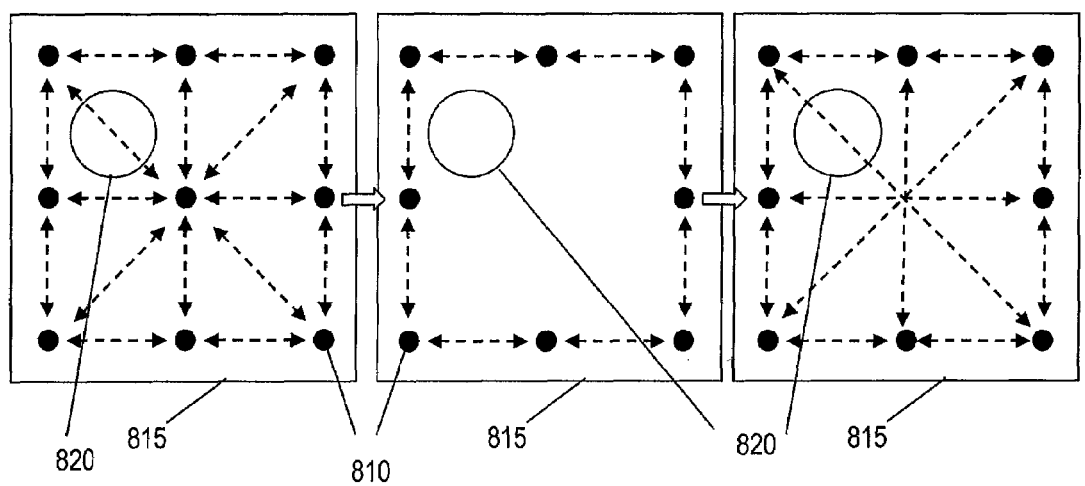

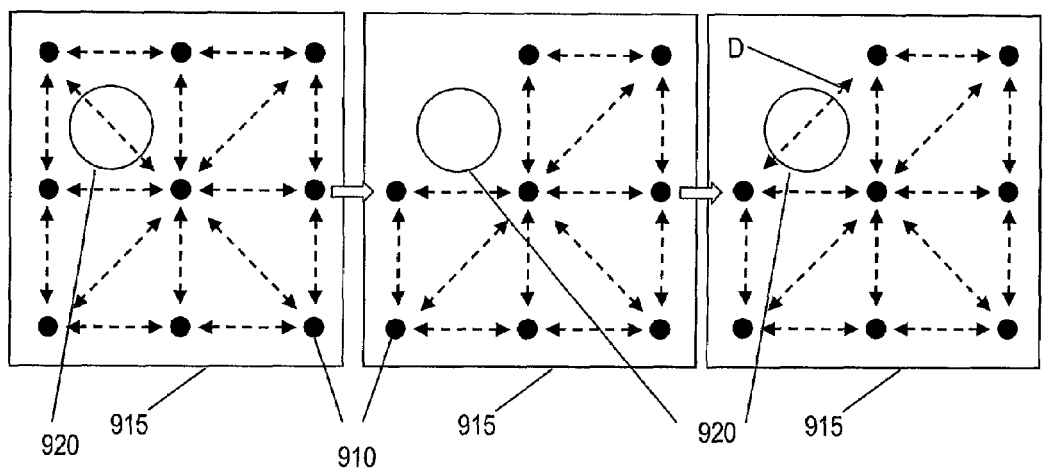
*Fig. 9A*  *Fig. 9B*  *Fig. 9C*

ROBUST DAMAGE DETECTION

CROSS-REFERENCE TO RELATED APPLICATION

This application claims the benefit of U.S. Provisional Patent Application Ser. No. 60/912,112, entitled "STRUCTURAL HEALTH MONITORING SYSTEM AND METHODS FOR USE," filed on Apr. 16, 2007, which is hereby incorporated by reference in its entirety.

TECHNICAL FIELD

This disclosure relates generally to structural health monitoring. More specifically, it relates to a reasoning methodology to improve the robustness of damage detection processes.

BACKGROUND

The diagnostics and monitoring of structures, such as that carried out in the structural health monitoring field, are often accomplished by employing arrays of sensing elements. The sensing elements are often used as both actuators and sensors. When damage occurs on the structure between the sensing elements the associated actuator-sensor paths become affected (show indications of damage). But there are other factors that can affect individual actuator-sensor paths, such as environmental changes, electromagnetic interference, sensor damage/degradation, etc. These other factors can cause false indications of damage. Therefore, a reasoning methodology is helpful to determine if effects observed on the actuator-sensor paths are caused by structural damage, transducer damage, or other factors.

SUMMARY

In one embodiment, a method of improving damage detection in a structural health monitoring system includes obtaining a baseline set of signals corresponding to a range of values of an environmental effect variable for a plurality of first selected paths between pairs of a plurality of transducers configured in an array attached to a structure. Threshold levels are established for each of the selected paths for determining detection of damage in the structure based on differences in the baseline set of signals for the selected path. A current signal is acquired for each of the selected paths. The plurality of current signals are analyzed based on the threshold levels to detect damage in the structure.

In another embodiment, a system for damage detection in a structural health monitoring system includes a one or more transducers configured in an array attached to a structure, a computer system further comprising a processor, memory and display, an interface to operably couple the computer system to the array, and a one or more software modules in the memory for determining on the basis of the baseline and current signal data if damage is identified in the structure.

BRIEF DESCRIPTION OF THE FIGURES

FIG. 7 illustrates a configuration of three transducers for detecting disbanding according to an embodiment of the disclosure.

FIGS. 8A-8C illustrate new path generation according to an embodiment of the disclosure.

FIG. 9 illustrates new path generation according to another embodiment of the disclosure.

Like element numbers in different figures represent the same or similar elements.

DETAILED DESCRIPTION

There are many factors that may add inaccuracy to a structural health monitoring system and cause changes that affect individual actuator-sensor paths. Some of the inaccuracy may be eliminated by calculating an index value (which is a measure of signal change) and comparing it to a preset threshold for each actuator-sensor path. Also, some changes may be compensated through environmental calibration techniques and sensor self-diagnostics. But to distinguish detection of structural damage from all other effects, such as environmental change effects and sensor damage, a reasoning methodology may be employed.

An exemplary method for calculating an index value and determining a threshold on the basis of the calculation is presented as Appendix A. The example uses temperature as an independent environmental variable and waveforms of signals transmitted between transducers forming selected paths corresponding to the temperature are collected. However, other environmental effects may be considered, such as humidity level or moisture content in a graphite/epoxy structure, changing compressive or tensile load (either hydrostatic or tensor), strain, or pH. The environmental effects indicated are exemplary and not intended to be limiting.

After the thresholds for each path have been established and sensor self-diagnostics have been performed, the signal data may be analyzed to find damage in the structure. A reasoning process may be used to eliminate false positives by analyzing data from paths that exhibit high index values (values above the threshold, discussed below) in the first arrival windows. The locations of these paths, along with their relative location to paths that exhibit high index values in the reflections, are used in the reasoning process.

Figure 1:
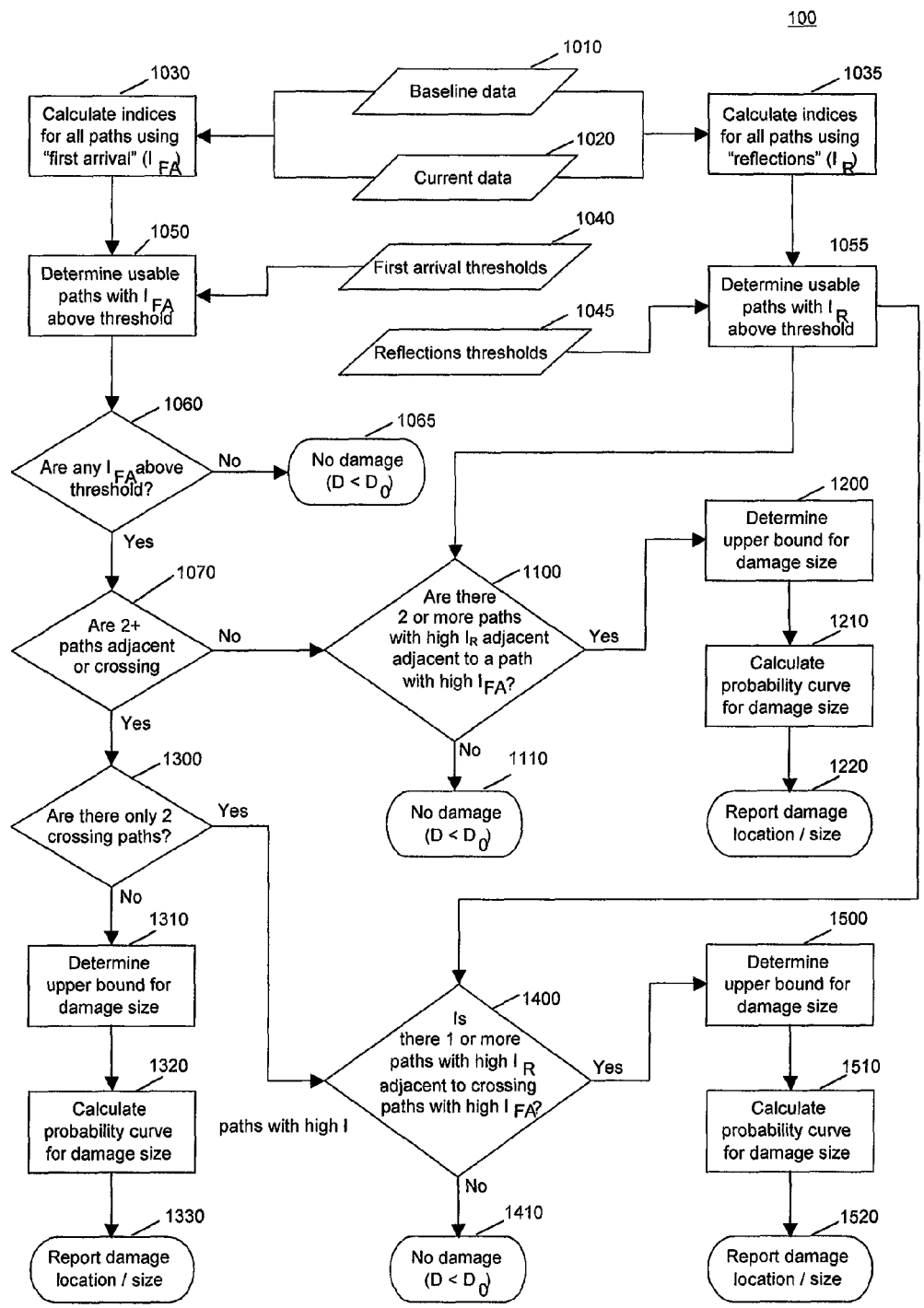
FIG. 1 illustrates a method of analyzing data in a structural health monitoring system to improve damage detection, according to an embodiment of the disclosure.

In an embodiment of the disclosure, FIG. 1 illustrates a method 100 of analyzing data in a structural health monitoring system to improve damage detection. A baseline data space 1010 comprises a set of data waveforms obtained from the structural health monitoring system. The baseline data space 1010 is constructed of sets of data waveforms representing data acquired, for example, at various values of one or more changing environmental effects.

The structural health monitoring system may comprise an array of a plurality of transducers attached to a structure. For example, the transducers may be piezoelectric and may excite elastic waves that propagate in the structure. Signals may be generated by a first transducer and detected by a second transducer, specifying a selected path. A first arrival signal may be defined as the portion of the signal corresponding to direct (i.e., not reflected) transmission of an elastic wave from one transducer to another. A reflection signal may be defined as a portion of the signal containing a reflection from a damage (or other) site not directly along the selected path, and therefore delayed in arrival time relative to the first-arriving signal.

In the absence of damage in the structure, different signals transmitted between the same pair of transducers may differ primarily in the arrival time of the transmitted elastic signal (and to a lesser extent, the amplitude), due to changes in the environmental variable. A baseline data set of waveforms 1010 can be generated for each selected path between pairs of transducers, each baseline waveform corresponding to a range of values of the environmental effects. For example, a waveform can be sent between pairs of transducers, at various ambient temperatures, establishing baseline profiles of the waveforms at various values of temperature.

A self-determining threshold may be found for each path as a determinant of damage identification. This may include a first arrival portion threshold 1040 and a reflection portion threshold 1045. For example, one or more "baseline" waveforms can be recorded and stored for each path between pairs of transducers. These baseline waveforms represent the state of the structure at the time the waveforms were recorded, before any additional damage is taken. An index representing the difference between one baseline waveform (which can be termed a reference baseline waveform) and all other baseline waveforms for a selected path may be calculated. Various methods of determining an index are possible. For example, a cross correlation of the reference baseline waveform to all other baseline waveforms results in a set of correlation time shifts, i.e., the difference between the arrival time of the reference baseline waveform and the arrival time of the other baseline waveforms. Setting a threshold based on the smallest, next smallest, etc., time shifts is one example. Alternatively, a Euclidean distance calculation of the waveforms relative to the reference may be calculated, and the threshold determined on the basis of selecting one of the resulting distance values obtained. The Euclidean distance calculation is well known in the art. Other index measures may be employed, and the above listed methods are not limiting. Thus, using only the baseline data, in the absence of damage, a threshold for damage detection may be set. This threshold may differ from path to path.

Once the baseline data waveforms have been collected and thresholds determined, the transducers can query the structure to determine whether any new damage has occurred. This new, or "current" data 1020 may be acquired as waveforms using the structural health monitoring system and a "best fit" match found between the current data and one of the baseline waveforms for the selected path. The "best fit" may be determined in numerous ways. For example, the "best fit" may be the defined as the closest waveform overlap between the first-arriving portion of the current data signal and one of the baseline waveforms for that path. In the presence of damage in the selected path, the amplitude of the current data waveform may be attenuated relative to the "best fit" baseline, however, the matched baseline waveform is still the "best fit" with regard to offsetting effects other than structural damage.

An index descriptive of the current data relative to the "best fit" baseline data for the first arrival portion of the signal data may be calculated (block 1030), i.e., $I_{FA}$, for each selected path, and a similar index for the reflection portion of the signal data, i.e., $I_R$, may also be calculated (block 1035). The index $I_{FA}$ may be calculated in the same manner as described above for baseline data, except that, for each path, the current data is compared to the "best fit" baseline data. For the case of the reflection portion, for example, a "best fit" may first be found for the first arrival portion, then the reflection portion of the waveform may be shifted to overlap with the "best fit" baseline first arrival portion and the index $I_R$ calculated on the basis of the difference in overlapping waveforms between the "best fit" baseline waveform and the time-shifted reflection segment. Values of $I_{FA}$ and $I_R$ may be obtained from current data for all selected paths. Different threshold values may be selected for $I_{FA}$ and $I_R$.

An exemplary method for locating the first arrival signal, i.e., the elastic wave pulse that propagates along a direct path between two transducers, is presented in Appendix B. The method may be equally applied to identifying the time of arrival of reflection signals from damage sites not located on the propagation path.

The $I_{FA}$ values for each path are compared to the corresponding threshold values for that path (decision block 1060). If a path has a high $I_{FA}$ value (e.g., greater than the selected threshold value), then it is considered a possible candidate for damage. If there are no paths that exhibit $I_{FA}$ values above the threshold (a No result in decision block 1060), then it is determined that no damage is present (terminal block 1065). Alternatively, if $I_{FA}$ exceeds some selected maximum limit, the damage may be due to defective transducers, as opposed to damage in the structure. In that case, alternative paths may be defined which provide substantially equivalent coverage for monitoring the structure, and data corresponding to damaged transducers may be deleted or ignored (block 1050, further discussed below). Appendix C includes an exemplary method for treating defective or disbanded transducers and defining alternative paths (i.e., "self healing") to maintain substantially full coverage for structural monitoring.

For the paths that exhibit $I_{FA}$ values above the threshold (a Yes result in decision block 1060), damage may be present, and a check is made to determine if there are two or more paths adjacent or crossing wherein one or more of the indices exceed the threshold for the selected path (decision block 1070). If the paths are adjacent (a Yes result in decision block 1070), then adjacent paths are checked for high $I_R$ values, i.e., values above reflection thresholds (decision block 1100). If there are fewer than two adjacent paths with high $I_R$ values adjacent to a single path with a high $I_{FA}$ value (a No result in decision block 1100), then no damage is present (terminal block 1110). The basis for this is that if damage is present, then the index $I_R$ must exceed the reflection threshold for both adjacent paths to confirm damage.

If there are two or more adjacent paths with high $I_R$ values adjacent to a single path with a high $I_{FA}$ value (a Yes result in decision block 1100), then damage is determined to be present. Thus, damage is confirmed by detection of reflection indices $I_R$ in both adjacent paths. In this case, a determination may be made of the upper bound of damage size (block 1200) by determining the largest circle that intersects the single path having a high $I_{FA}$ but does not intersect adjacent paths. That is, the adjacent paths have waveform signals indicating a (delayed) reflection signal but not a first arrival. A probability of detection curve may be calculated for various sized damage (block 1210). Probability of detection (POD) curves are well known in the art. Based on the location of the paths and the POD, a report may be issued indicating location and probable damage size (block 1220).

Returning to decision block 1070, if the paths having high $I_{FA}$ are crossing, it may occur that there are more than two crossing paths, in which case, damage may be determined to exist (a No result in decision block 1300) since any damage that is detected by high $I_{FA}$ in more than two crossing paths is a strong indicator of extensive damage. In this case, a determination may be made of the upper bound of damage size (block 1310) in a manner similar to that just described, i.e., by determining the largest circle that intersects the two crossing paths having a high $I_{FA}$, but does not intersect adjacent paths. A probability of detection curve may be calculated for various sized damage (block 1320). Based on the location of the paths and the POD, a report may be issued indicating location and probable damage size (block 1330).

If there are only two crossing paths with high $I_{FA}$ (a Yes result in decision block 1300), a determination may be made whether there are one or more adjacent paths with a high $I_R$ value (decision block 1400). If there are no adjacent paths indicating high reflection index $I_R$ (a No result in decision block 1400), then no damage may be determined to be present on the selected path with a high $I_{FA}$ (terminal block 1410). That is, the absence of indices $I_R$ greater than the reflection index threshold is an indicator that a supposed damage is not severe enough to produce a reflection signal. The implication is that the high $I_{FA}$ may be due to transducer disbonds, malfunctions or other causes, but not due to structural damage. If, however, there are one or more adjacent paths with a high $I_R$ adjacent to two crossing paths with high $I_{FA}$ (a Yes result in decision block 1400), then damage may be determined to exist. In this case, a determination may be made of the upper bound of damage size (block 1500) in the manner described above, with respect to the two crossing paths and the two adjacent paths. A probability of detection curve may be calculated for various sized damage (block 1510). Based on the location of the paths and the POD, a report may be issued indicating location and probable damage size (block 1520).

The following summarizes the various criteria for determining damage is detected, using the rules of the reasoning process:

1 path with a high $I_{FA}$ value and 2 or more adjacent paths with a high $I_R$ values.

2 crossing paths with high $I_{FA}$ values and 1 or more adjacent paths with a high $I_R$ value.

2 or more adjacent (not crossing) paths with high $I_{FA}$ values.

If an actuator-sensor path exhibits changes and it is determined that the changes are caused by something other than damage, then an adaptive process can be used to maintain overall functionality of the system. All signal data from paths corresponding to faulty transducers may be removed from the analysis routines, and data from additional paths may be automatically added to cover the same area as shown in FIG. 1. Self-diagnostic methods, wherein the electrical impedance characteristics of transducers are evaluated with respect to reference characteristics may, for example, be used to remove faulty transducers and any associated data from the structural health monitoring system. To provide equivalent coverage of the structure, i.e., the ability to detect damage down to at least the same size as before, additional path(s) between other combinations of operational transducers may be added (e.g., automatically or manually). This determination of usable paths may be made, for example, in block 1050 based on first arrival signal data, and in block 1055 based on reflection signal data.

Determination of usable paths resulting from transducer defects may be accomplished in numerous ways. For example, measuring the impedance of each transducer may be used to find an open or short circuit. This may indicate the transducer is missing or there is a damaged wire connection. Disbonded transducers, i.e., transducers that are electrically intact and functional, but are not attached to the structure, may be detected by a process of testing pitch-catch signal transmission between a sufficient number of pairs of transducers to determine the integrity of the bonds, as disbanded transducers may neither excite nor detect elastic waves propagating in the structure. The methods of testing the integrity of the transducers and/or bonding to the structure are intended to be exemplary, and are not intended to be limiting in scope.

Figure 2:
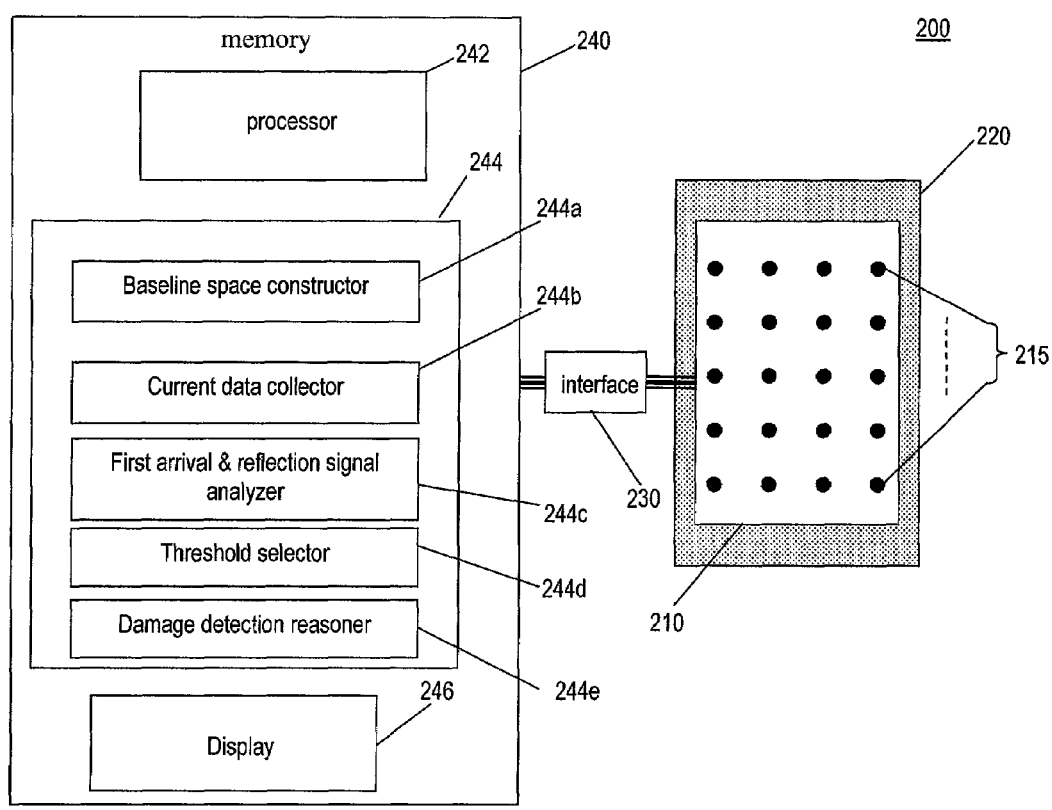
FIG. 2 illustrates a system for analyzing data in a structural health monitoring system to improve damage detection, according to an embodiment of the disclosure.

FIG. 2 illustrates a system 200 for analyzing data in a structural health monitoring system to improve damage detection, according to an embodiment of the disclosure. System 200 comprises an array 210 of transducers 215 attached to a structure 220 to be monitored for damage. Array 210 is operably coupled to an interface 230 for communication of signals and data to a computer system 240. Computer system 240 comprises a processor 242 and a memory 244 and may further comprise a display 246, which may be internal or external to computer system 240. Processor 242 operates a plurality of software modules (described below), which may be stored in memory 244. In addition, memory 244 may receive data from array 210 and various software modules, described below, for the objective of detecting damage in structure 220.

In one embodiment, transducers 115 may be piezoelectric actuator/sensors capable of exciting and detecting elastic waves which propagate from one transducer and may be detected by one or more other transducers in array 110. Transducers 115 may be operated in a pulsed mode, i.e., where a short burst electrical signal excitation produces a resonant elastic response, wherein the elastic response is coupled to the structure. Elastic waves may then propagate uniformly in all directions, or transducer 115 may be configured to propagate elastic waves in preferred directions. For example, where defects manifest as surface breaking cracks in structure 120, the elastic waves generated are preferably surface elastic waves that propagate in all directions on the surface, and are therefore detectable by a plurality of transducers 115 of array 110. Other configurations of array 110 may be implemented, for example, where elastic waves are transmitted from a portion of array 110 through the volume of structure 120 and detected by transducers 115 in another portion of array 110, thereby detecting embedded flaws.

A baseline space constructor 244a is a software module for acquisition of signal data from transducers 215 of array 210 and arranging the data according to, for example, selected paths between transducers 215, and values of variables dependent on environmental effect changes. A current data collector software module 244b may obtain data in a similar fashion under conditions of structural health monitoring, i.e., when the structure is being monitored for the occurrence of damage. A first arrival and reflection signal analyzer software module 244c may segment the signal data acquired using baseline constructor 244a and current data collector 244b to identify first arrival signal portions and reflection signal portions in the signal data. A threshold selector software module 244d may analyze the baseline data and select threshold values based on that data for determining whether the first arrival portion and/or reflection portion of the current signal data implies the existence of damage associated with the selected paths from which the data is acquired. A damage detection reasoning module 244e compares the signals in crossing and adjacent paths on the basis of the threshold values selected, to determine if damage is identified, the location of the damage, size of the damage, and probability of detection.

Having thus described embodiments of the present disclosure, persons of ordinary skill in the art will recognize that changes may be made in form and detail without departing from the scope of the invention, which is limited only by the following claims.

Appendix A

Figure 3:
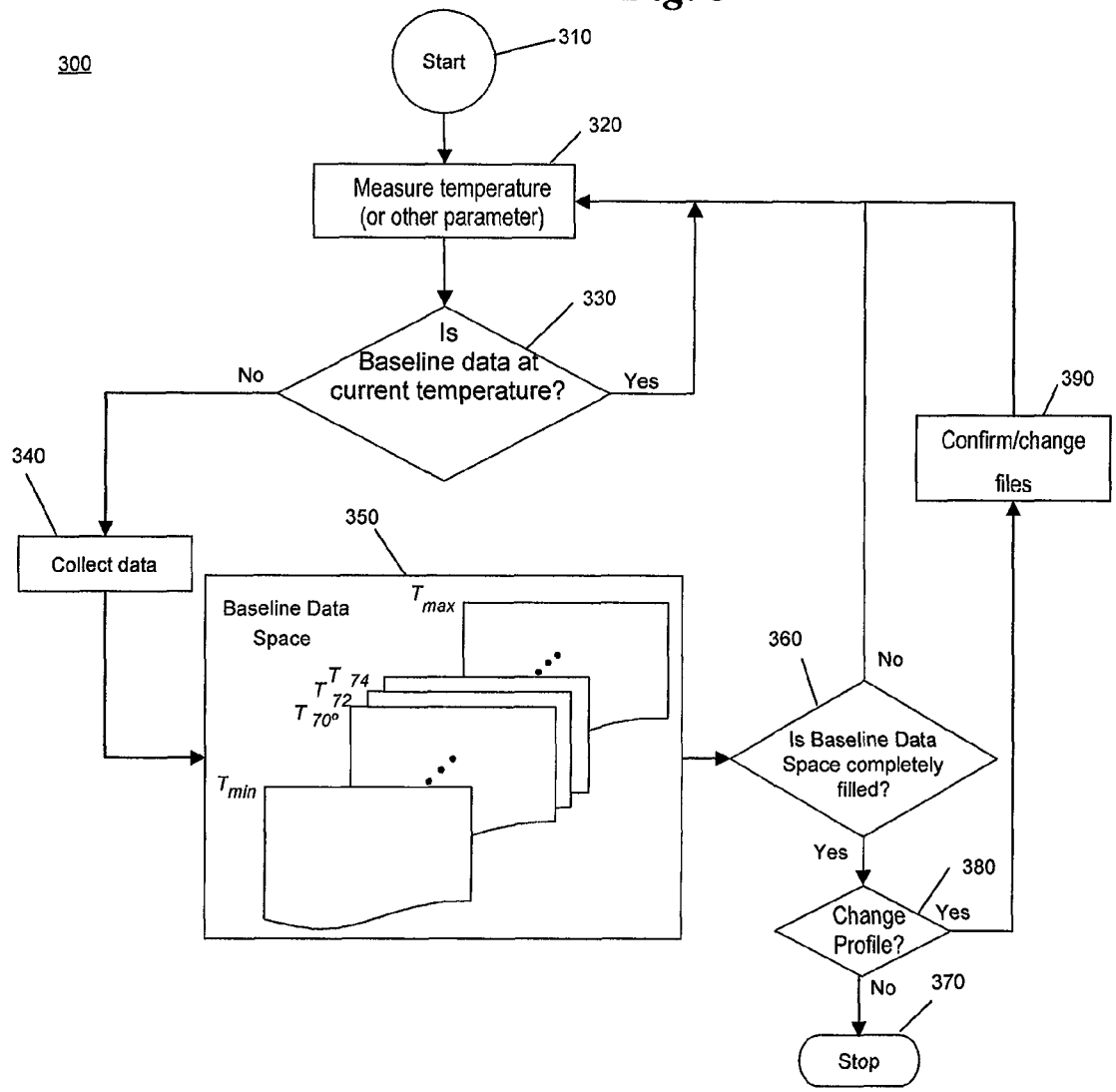
FIG. 3 shows a calibration method for establishing a baseline set of data according to an embodiment of the disclosure.

FIG. 3 shows an embodiment of a calibration method 300 for establishing a baseline set of data of the performance of a transducer array attached to a structure as part of a structural health monitoring system.

One or more temperature sensors (not shown) may be attached to structure 220, preferably in proximity to transducers 215 of array 210 or selected paths between transducers 115. Equivalently, stress, strain or moisture sensors may be used. The transducers 215 may be, for example, piezoelectric, magneto-elastic, electrostatic or any other suitable elements adapted, when attached to structure 220, to excite and/or detect elastic waves in the body or on the surface of structure 220. In the embodiment being described herein, it is assumed that the structure initially has no detectable damage. Once started (block 310), calibration method 300 proceeds to acquire temperature readings (block 320) at selected locations on structure 220. Hereinafter, it may be assumed that array 210 and structure 220 are at substantially the same temperature at least at each respective location of the one or more temperature sensors. However, this is not a requirement, and the temperature at each of the selected paths may be different, provided they can be measured.

In Start block 310, temperature measurements may be user defined, e.g., they may be made at selected values, or may be made at temperatures of one or more specified increments over a range from a minimum temperature $T_{min}$ to a maximum temperature $T_{max}$. These parameters for acquiring calibration data may be selected, for example, via a graphical user interface provided by a temperature calibration control program. For example, as indicated above, the user may enter $T_{min}$, $T_{max}$, and temperature increments $\Delta T$, and a stabilization dwell time $\Delta t$, i.e., a delay time between setting temperature and when the measurement is made to provide a temperature stable measurement of signals. $\Delta T$ may be a fixed or unevenly spaced temperature interval.

Alternatively, for example, $\Delta t$ may be a time interval such that the recorded temperature must remain within 1° C. of the desired calibration temperature before collecting a set of baseline data. Thus, the temperature interval $\Delta T$ and/or the dwell time $\Delta t$ may be selected dynamically based on continuous monitoring of the temperature. Alternatively, measurements may be made at arbitrary temperatures, and data sets may be repeatedly acquired until an adequate specified temperature range and value variations have been satisfied. A change profile decision block 380 will be discussed below.

If baseline data has previously been obtained at a given temperature (a Yes result in decision block 330), method 300 returns to block 320, and measurement is iterated until a different temperature is obtained. Temperature may be controlled from an external source, or temperature changes may occur through natural environmental (e.g., cyclic) processes. For example, a bridge or a building may undergo diurnal temperature cycles, so that $\Delta t$ may be on the order of hours. In another example, a satellite in full sunlight may have components with a rotation period of several minutes, so that $\Delta t$ may be on the order of several seconds to minutes.

In addition, as a satellite revolves around the earth (e.g., in approximately 90 minutes) and spends approximately half that time in the earth's shadow, thermal load cycling may result in an additional $\Delta t$ that may be on the order of several minutes. When a different temperature reading from among the selected temperature values is returned from the one or more temperature sensors (a No result in decision block 330), computer 240 proceeds to collect data (block 340) comprising signals transmitted along paths selected between pairs of transducers 215 of array 210 that provide a required degree of coverage for later detection of damage on structure 220.

The data corresponding to all selected actuator-sensor paths at a given temperature (or within a specified temperature range) is assembled into a data file and stored (block 350) in a baseline data space in machine readable memory 244 of computer 240. If the baseline data space is not completely filled, i.e., data is not yet acquired for all specified temperature values (a No result in decision block 360), method 300 returns to block 320 to make another temperature measurement until a new temperature, not previously obtained, is detected. If the baseline data space is completely filled, i.e., values have been obtained and data has been acquired (a Yes result in decision block 360) for all temperatures and paths, method 300 checks to see if the baseline data space is complete, and if a profile change of measurement conditions are desired. If no change in the measurement profile is required (a No in decision block 380), the method stops (block 370).

After completion of the temperature calibration method 300, the user may wish to modify the data sets for various reasons and acquire data under changed measurement conditions (a Yes result in profile decision block 380). For example, some data sets, which may correspond to data acquired at certain temperature readings, may no longer be valid, or may have noise or reading errors. Therefore, the user may wish to confirm the data (block 390), which may require repetition of a measurement under a certain environmental condition. Additionally, the user may decide, for example, to add additional increments of temperature, change the temperature range, or discard certain files, either because of data error, changes in the calibration profile, or other reasons. A Yes decision in block 380 forwards the method to a review process (block 390) to confirm and/or alter the calibration parameters, alter files (e.g., delete) and then returns operation of method 300 to continue the measurement loop at block 320.

Figure 4:
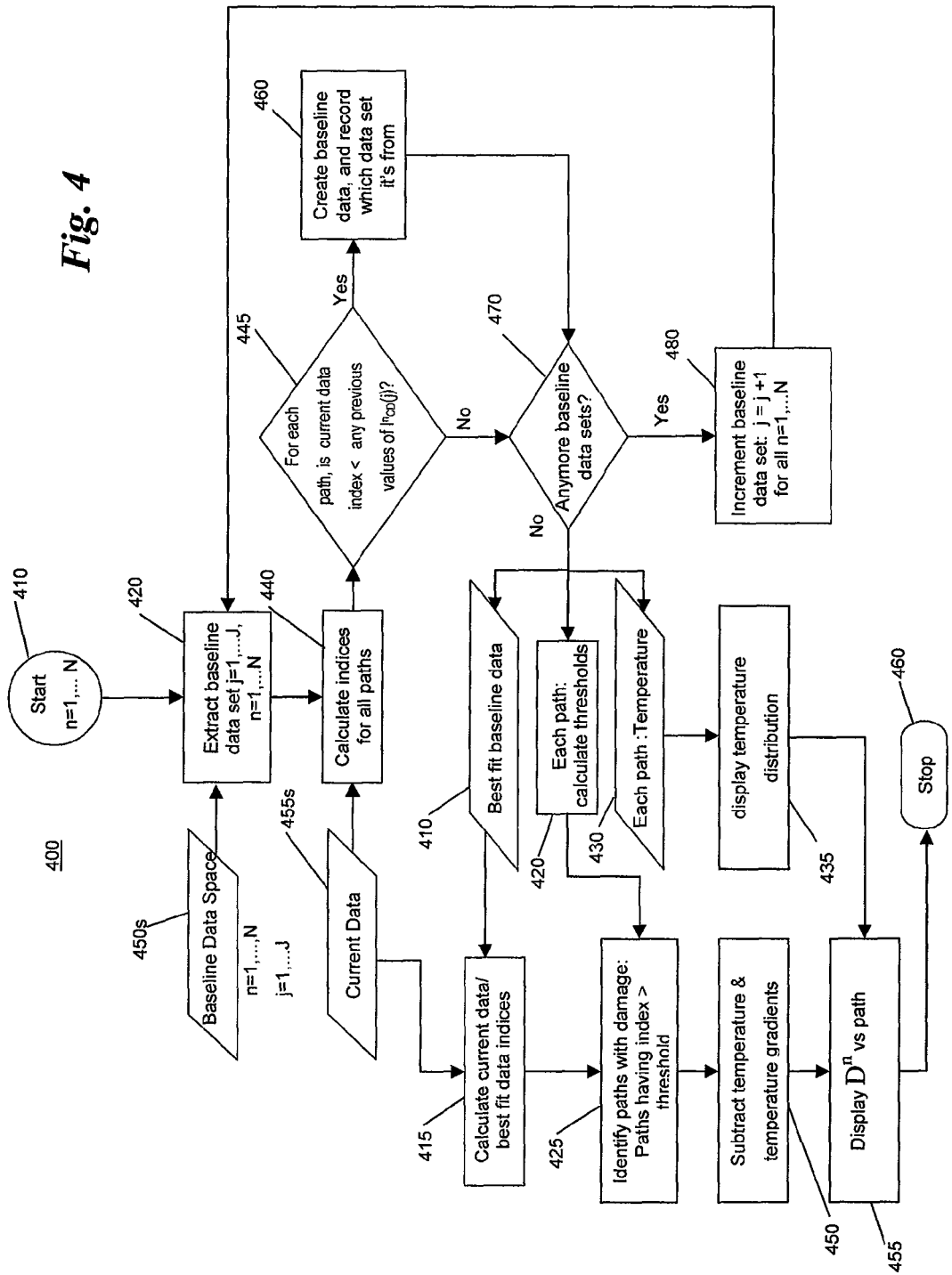
FIG. 4 illustrates a method of compensated data signal detection according to an embodiment of the disclosure.

When the baseline data space is completed, a compensated data signal detection method 400, shown in FIG. 4, may be implemented. Method 400 fits detected current signal data to the best fit with data obtained in calibration method 300. This best fit approach effectively yields the temperature of the structure along each path when temperature sensors may not be available or functional during actual health monitoring operational conditions. After a scan of structure 220 is performed—which may now potentially include damaged areas, the newly recorded signals (current data 455s) for each path are compared to the corresponding baseline space data sets 450s to determine a best fit for data at various temperatures. Temperature for the corresponding actuator-sensor path is determined according to this best fit, as indicated above, as well as identifying the baseline data set to be used for damage assessment. Method 400 may then detect changes due to damage relative to the best fit baseline data set. In the present embodiment, for simplicity of discussion, the structure may be assumed free of defects during temperature calibration and the baseline data space represents a reference for all subsequent measurements monitoring for damage detection within the specified temperature range.

Baseline data space 450s includes N paths (i.e., n=1, ... N) selected from array 210. In each selected path, a data signal corresponding to each of J selected values (i.e., j=1, ... J) of the environmental parameter (e.g., temperature) is included in baseline data space 450s. Referring to FIG. 4, method 400 starts (block 410) with a call to extract a first baseline signal data set (block 420) from baseline data space 450s (stored in block 350 of method 300) corresponding to the n=1th path, j=1st temperature value (or other environmental parameter value) which has been stored and maintained in machine readable memory 244. Using temperature as an example of an environmental parameter, start 410 assigns a counter j=1, . . . J to the J baseline signal data sets in baseline space corresponding to the number of temperature values selected for a selected path n, and initializes j=1. For each selected path n of N paths, the data files in baseline data space 450s are selected one at a time according to the current value of j in block 420 and is compared with the current data set obtained for the same path n.

Current data 455s includes signal data sets corresponding to signals transmitted along the N selected path, which now may or may not contain a damage defect. Since baseline data space 450s is complete, current data 455s may now be acquired and temperature compensated detection of damage may proceed (described below).

Figure 5:
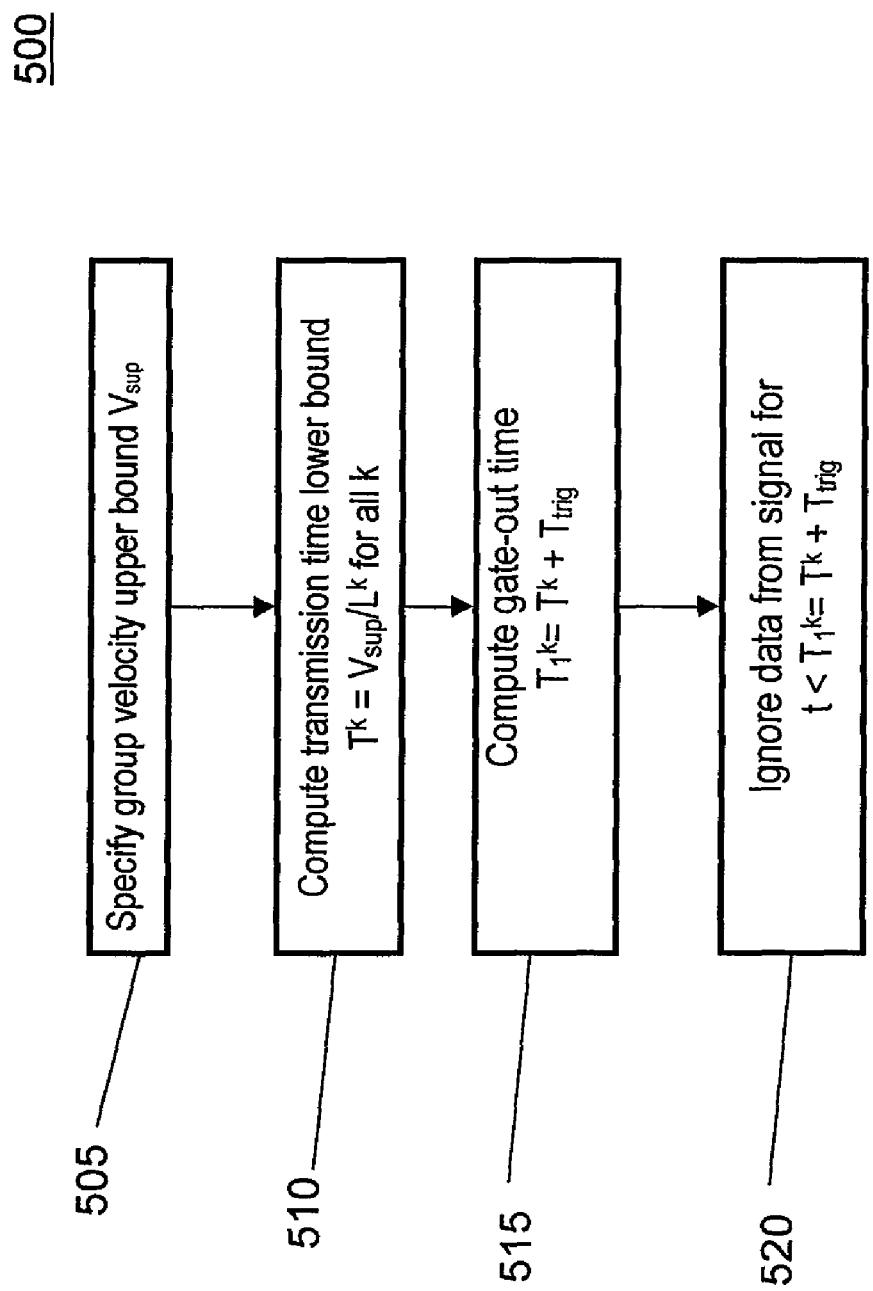
FIG. 5 illustrates an exemplary graph of first arrival baseline index values according to an embodiment of the disclosure.

For a given selected path n, one baseline signal data set (n,j) from baseline data space 450s may be chosen as a reference. For example, a reference baseline signal data set may be a signal acquired, for the selected path, at substantially the midpoint of the operational temperature range of the structural health monitoring system, although other reference points may be chose. All remaining baseline signal data sets may be compared to the reference baseline signal data set as follows: A single baseline signal data set for a selected path n comprises a waveform $X''0$ that may be represented as a vector $X''0(j) = \{X''0(j), \ldots X''0_m(j), \ldots X''0_M(j)\}_j$, where j refers to the jth value of temperature (or other environmental effect variable value), and $X''0_1(j), \ldots X''0_m(j), \ldots X''0_M(j)$ are M discrete values of a jth digitized record of the signal in the data set for the nth selected path. For simplicity, j=1 may be taken as identifying the reference temperature. All baseline signal data sets may be compared to the reference baseline data set by calculating a relative index—a baseline index $I_{BL}(j)$—for each baseline signal data set given, for example, by $$I_{BL}^n(j) = \frac{\sqrt{\sum_{m=1}^{M} (X0(j)_m - X0(1)_m)^2}}{\sqrt{\sum_{m=1}^{M} (X0(j)_m + X0(1)_m)^2}}, \quad (1)$$

where, for convenience, the superscript n in $X''0(j)$ and $X0n$ (1) have been left out of the equation but is implied. It is noted that when j=1, i.e., j identifies the reference baseline signal waveform, $I_{BL}''(j)=0$, as expected, i.e., there is no difference between the baseline waveform being tested and the reference waveform. All baseline signal data waveforms acquired at temperatures increasingly distant from the reference temperature will result in a baseline index $I_{BL}''(j)$ that increases correspondingly. FIG. 5 shows an exemplary graph of baseline index values $I_{BL}(j)$ for a given actuator-sensor path according to an embodiment of the present disclosure.

The properties of $I_{BL}''(j)$ enable a threshold to be selected for each of the n paths on the basis of temperature (or other environmental effects) independent of details of the structure, signal levels in other paths, or other structure or system specific factors. For example, with reference to FIG. 5, the nearest neighbor value of $I_{BL}''(j)$ may selected as a threshold value, the application of which will be described in more detail below. Alternatively, $2^{nd}$ or $3^{rd}$ nearest neighbor values may be selected instead. As will be seen, a smaller value of selected threshold implies more sensitivity in the detection of damage signals, whereas a larger selected threshold implies less sensitivity. Note that every one of the n paths may have a unique threshold regardless of the selected sensitivity parameter, since the indices of different selected path data sets are independently obtained.

Returning to FIG. 4, as described above, when baseline signal data set (n,j) is extracted (block 420) from baseline data space 450s, the relative baseline indices $I_{BL}''(j)$ may be calculated (block 440) for all paths. Current data 455s may be acquired for each of the n paths, and current data indices $I_{CD}''(j)$ relative to the j baseline signal data sets for path n may be computed, for example, in a fashion similar to that described above, given by:

$$I_{CD}^n(j) = \frac{\sqrt{\sum_{m=1}^{M} (X0(j)_m - X_{CD_m})^2}}{\sqrt{\sum_{m=1}^{M} (X0(j)_m + X_{CD_m})^2}}, \quad (2)$$

where, again, the path selection superscript n is assumed for $X''0(j)$ and $X''0_{CD}, X_{CD_m}''$ is the mth value of M such digitized values in the current signal data waveform, which may be represented, by analogy with $X''0(j)$, i.e., as a vector $X_{CD}''$, and $I_{CD}''(j)$ are the indices of the current signal data set computed relative to the baseline data set. One may note that when $X0(j)$ and $X_{CD}$ are identical, i.e., the waveforms have perfect overlap, then $I_{CD}(j)=0$, and an ideal match is found. Normally, however, this may not be the case, as various effects, such slight differences in the current and baseline temperature, signal noise, etc., in addition to damage, may result in differences in the measured current signal data waveform and any baseline waveform. However, seeking the minimum value of $I_{CD}''(j')$ obtains a best fit of current data to the j'th baseline signal data set, and concurrently identifies the best fit corresponding j'th temperature. This is explained in detail below.

Once the index $I_{CD}''(j)$ is calculated for the current data set (e.g., for the first temperature value, say j=1) for the path n (initially the n=1 path), a comparison must be made as to whether the current data index is less than or greater than any previously calculated current data index, i.e., $I_{CD}''(j-1)$. Since j=1 is the first time the calculation is being made, $I_{CD}''(j=0)$ may be set to an arbitrarily large value to insure that the first calculated current data index $(I_{CD}''(1)$ becomes a first reference value. Since the first calculated index will be less than any previous value (a Yes result in decision block 445) the baseline data set used to calculate the current index is entered in a new baseline data set (block 460), and represents a best fit to the current data.

In decision block 470, an inquiry is made whether all J data sets for the path n have been obtained from baseline data space 450s to calculate more current data indices. If more baseline date sets remain to be compared to the current data set for the path n (a Yes result in decision block 470), j is incremented (block 480), and the next baseline dataset (j+1, n) is extracted (block 420) to repeat the index calculation (block 440) of current data versus the next baseline data set. When all J datasets for path n are exhausted, n is incremented to the next path. In the subsequent calculation the newly computed current data index may be less than any previously computed index (for the current path n)—a Yes result in decision block 445. In this case the current data set is a better fit to the j+1th baseline data set, and the j+1th baseline data set replaces the last baseline data set entered as the previous best fit.

In this loop, as described, block 460 creates a data base comprised of the single best fit baseline data sets corresponding to the current data sets 455*s*, which have been acquired by the health monitoring system for each of the N selected paths. When there are no more baseline data sets (i.e., all J data sets for all N paths have been examined for best fit)—a No result in decision block 470, method 400 proceeds to examine the relationship between the current data and the best fit baseline data to determine the temperature corresponding to the selected paths, compensate the data in terms of the best fit current data indices and identify the existence of damage in terms of the indices, as will now be described below.

The best fit baseline data selected in the previous steps (and accumulated in block 460) may be organized as follows: The resulting best fit baseline signal data may be stored in data block 410. For each selected path in block 420 the best fit baseline indices $I_{BL}(j)$ may be calculated and threshold values (whether nearest, next nearest, etc., neighbor values) of $I_{BL}(j)$ are chosen, for example, as describe in relation to equation (1). However, a threshold value of index may be chosen using other methods, including, for example, specifying an arbitrarily chosen numerical value for $I_{CD}{}''$, which may be based on prior measurement experience. A data set 430 of temperatures corresponding to each of the best fit baseline signal data sets is formed corresponding to each path. Data blocks 410 and 430, and step 420 are provided for all selected paths in the structural health monitoring system. The temperature data set 430 may be displayed (block 335) as an array corresponding to the selected paths of the structure 220.

Under operational conditions of the structural health monitoring system, current data 455*s* may be acquired and compared to best fit baseline data 410 to calculate indices (in block 415) for best fit of the current data to the baseline data, $I_{CD}(j)$, using the prescription of eq. (2) and seeking the value j' for which $I_{CD}(j')$ is a minimum. In this manner, the "best fit" value j' of the environmental variable may be determined and used in subsequent damage detection. As distinguished from earlier calculations of $I_{BD}(j)$, where baseline data sets were being established, and a threshold value of the index is selected based on the change in index value for corresponding adjacent temperature values, now the possible existence of damage in the selected path of the structure may result in a set of indices $I_{CD}(j)$ for some paths that have a similar appearance as in FIG. 5, but are shifted upward, in recognition that new data differs from baseline data by the presence of damage.

In block 415 the current data set is compared to the best fit baseline data set (for the nth path) by examining the index value for the current data set relative to the best fit baseline data set. The current data indices obtained in block 415 are compared with the thresholds obtained in block 420 to identify paths with damage (in block 425) as follows: A difference $D''=I_{CD}{}''(j')-I_{BL}{}''(j_{TH})$ is calculated for the selected path, where, again, $I_{CD}{}''(j')$ is the best fit current data index, and $I_{BL}{}''(j_{TH})$ is the index chosen from baseline data as the threshold, all for path n. If $D''$ is positive, the best fit current data has an index that exceeds threshold and determines that there is damage in the path, and the level of damage may be indicated by assigning a value of, for example, $D''$ or $I_{CD}{}''(j')$. If $D''$ is equal to or less than zero, the best fit current data index does not exceed the threshold and determines that there is no damage detected. The absence of detected damage is indicated by assigning a value of zero.

By identifying damage in terms of the difference $D''$ of the current data index and the threshold, temperature and temperature gradient effects are automatically removed from the data (block 450), i.e., the data is compensated for environmental effects.

All assigned values of damage level (whether $D''$, $I_{CD}(j')$ or zero) may be assembled into an array corresponding to the N selected paths of structure 220 (block 455). The assembled array of damage level values provides a representation of damage data (in block 350) with temperature and temperature gradient effects removed from the data. The assembled array of damage level values may be displayed concurrently with, or separately from, the display of temperature data set 430 as provided in block 435.

A pulse that scatters or reflects from a defect that is not inline will proceed along an indirect path, thus having a longer time-of-flight, and arrive later in time. This signal can be blocked and rejected, for example, by time-gating or digital filtering. Alternatively, additional signal processing methods may be applied to the delayed reflection signals to obtain further structural health information.

An embodiment of threshold selection may be understood as follows: The threshold value is selected based only on baseline data. One temperature may serve as a reference. All other baseline signal data sets are at temperatures offset relative to the reference temperature. Thus, a baseline signal data set at a first adjacent increment of temperature from the reference will have an index greater than that calculated at the reference temperature, and baseline data corresponding to further increments from the reference temperature will have correspondingly greater index values. When collecting data during structural health monitoring, current data may be considered to show evidence of damage if the minimum index calculated for current data is greater than the threshold selected on the basis of baseline data, and the value of the index may be plotted, for example, as a color coded map, where the color coding corresponds to the excess value of the index of the current data over the threshold index. Current data that results in an index that is below the selected threshold may be ignored, e.g., not plotted. Selecting a higher threshold reduces the probability of specifying that a damage site has been detected. Selecting a lower threshold introduces more noise in the plot. The invention contemplates the selection of any threshold.

A threshold value using reflections from damage defects that are not directly on the selected path is contemplated by the invention, and may be determined in the same way as those for the first arrival of inline signals, except that the time windows may be different. Furthermore, one of ordinary skill in the art will realize that the invention encompasses the use of any suitable index, including those of equations (1)-(2), as well as others. In particular, the invention contemplates determination of any index that allows for selection of a damage detection threshold without independent detection of an environmental variable. Additionally, one of ordinary skill in the art will also realize that the methods and apparatuses of the invention can be employed to compensate for any environmental variable, and not just to compensate for temperature effects.

Appendix B

Extracting the first arrival pulse (or a later reflected signal pulse) in an elastic wave signal may first require removal of electromagnetic interference (EMI) cross-talk since EMI may be detected at the receiving transducer with larger amplitude than the elastic wave signal.

FIG. 5 is a flow diagram of cross-talk removal 500, in accordance with an embodiment of the disclosure. A rough estimation of the upper bound of the elastic wave group velocity $V_{sup}$ may be supposed (block 505). Then, the lower bound of the transmission time is computed (block 510) as $T^k = L^k/V_{sup}$, where $L^k$ is the length of the kth path specified by two transducers. The time $T_1^k = T^k + T_{trig}$ may then be chosen (block 515) as the maximum time for gating out the cross-talk component, where $T_{trig}$ is the time at which the transducer was triggered to generate an elastic wave. Data in the signal corresponding to the kth path up to time $T_1^k$ may be ignored for further analysis (block 520). For example, this data may be replaced by null values, or alternatively, only data for time greater than $T_1^k$ may be used in the further analysis.

$V_{sup}$ can be selected or estimated from a large range of values. It is thus a relatively easy matter to select $V_{sup}$ and minimal knowledge about the structure is required. The choice of $V_{sup}$ may preferably be chosen to be somewhat less than the highest known actual group velocity in the structure. The resulting time interval $T_1^k$ may be used to define the minimum delay before a signal arriving at the receiving transducer (i.e., sensor) is measured to gate out the cross-talk.

Since the speed of EMI cross-talk is approximately five orders of magnitude greater than the group velocity of typical elastic waves, the time delay associated with the EMI interference may be assumed to be negligible, so that $V_{sup}$ may be somewhat arbitrarily chosen provided the resulting $T^k$ is at least greater than the time length of the trigger pulse, i.e. as long as the cross-talk does not substantially overlap with the first arrival signal. It should be noted that in the case where the cross-talk significantly overlaps with the first arrival, the damage detection may typically be unreliable since the amplitude of the cross-talk interference with the elastic wave signal detected may considerably change the shape of the acquired signal. Fortunately, in the health monitoring of large composite structures, where propagation delay may generally be comfortably greater than the trigger pulse width, this may usually happen very rarely.

After the process 500 for eliminating EMI, a second process—the first arrival detection process 600 may proceed. Two embodiments are disclosed herein.

Figure 6:
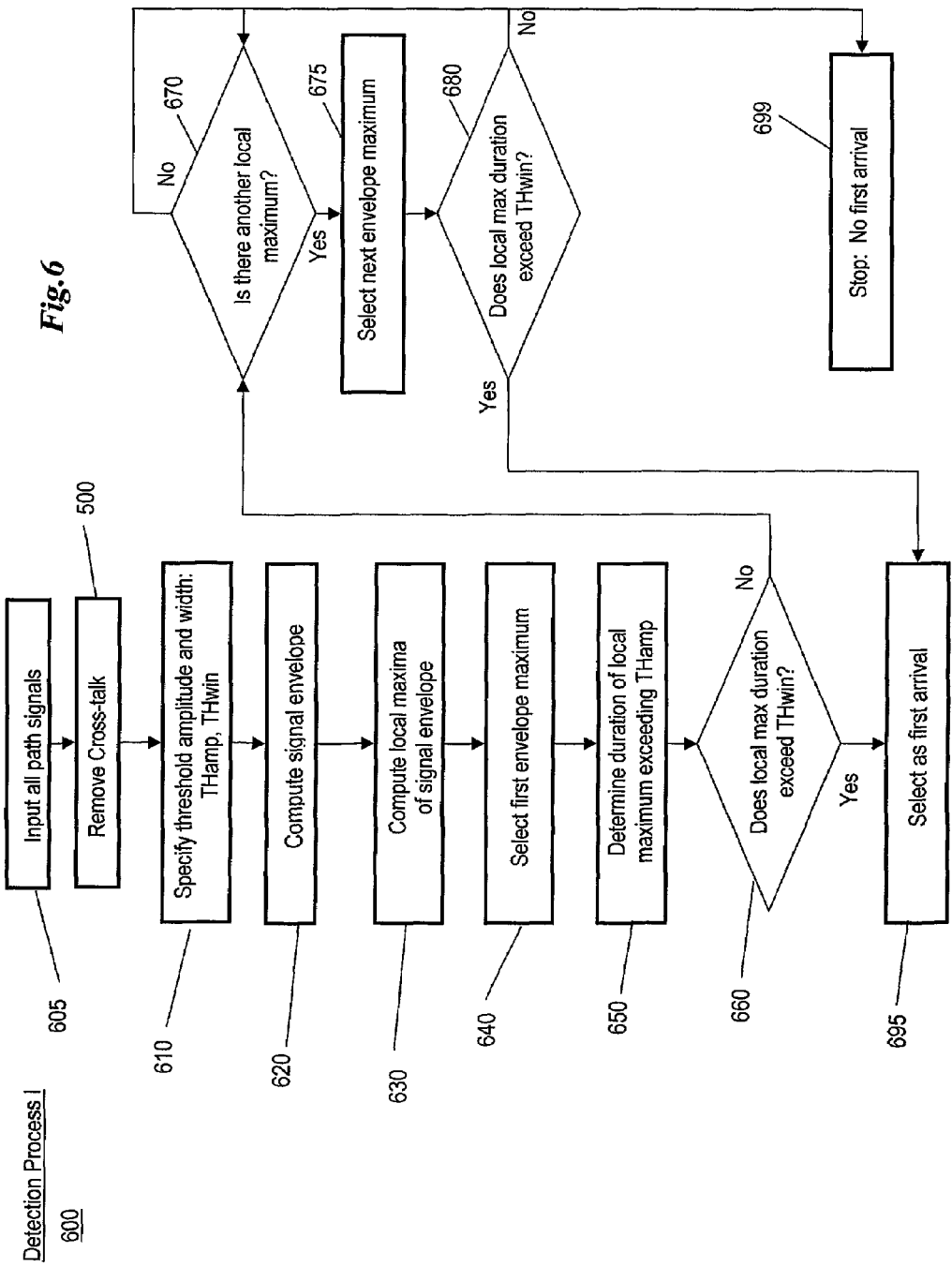
FIG. 6 illustrates a first arrival signal detection method according to an embodiment of the disclosure.

In one embodiment, FIG. 6 illustrates a flow diagram of a first detection method 600 that uses the envelope of the signal to detect the first arrival based on the amplitude and width of a wave packet. Method 600 includes inputting (block 605) to computing system 240 all signals from all paths specified between transducers 215 of array 210. Method 500 for removal of cross-talk may be applied to all signals. A threshold specification (block 610), in which a threshold amplitude THamp and a threshold window of time width THwin for the first arrival signal, is selected. THwin may be selected at least on the basis of the time characteristics of the exciting signal applied to the transmitting sensor and the response of the transmitting sensor to the signal, which may be affected by mechanical resonance, electrical impedance, for reasons that will be made apparent below.

The window THwin begins at a time t1 that is at least greater than $T_1^k$ and ends at t2=t1+THwin. The envelope of the signal detected at the receiving sensor may then be computed (block 620). Characterization of the envelope of the amplitude enables determination of the time at which the signal reaches or passes the amplitude threshold THamp, and the time width of the detected signal, as described below. Computing the signal envelope enables determination of all local maxima (block 630) in a signal waveform following the time t1. The signal waveform may then be analyzed to select the first local maximum (block 640) in the window.

The envelope is analyzed about this local maximum to determine the time duration (block 650) of the local peak as defined by the time during which the envelope exceeds the amplitude threshold THamp. The time at which this occurs is t1, as defined above, and is required to be equal or greater than the time $T_1^k$ for eliminating EMI cross-talk. The time duration determination in block 350 then seeks the point in time when the trailing edge of the signal envelope drops below THamp. If the time duration measurement (block 650) determines that the pulse width corresponding to the first maximum is broader than THwin (a Yes result in decision block 660) then the pulse is designated as a first arrival pulse, and the time of arrival is t1. If the pulse is narrower than THwin (a No result in decision block 660), then that pulse is not considered as a first arrival pulse, but may be noise, a weak signal or another artifact. In that case, the signal envelope is further examined to determine if there is another later local maximum (decision block 670).

If another local maximum in the envelope is found (a Yes result in decision block 670), this envelope local maximum is selected (block 675) and tested to determine if the peak exceeds THamp for at least the duration of THwin (a Yes result in decision block 680) or is narrower than THwin (a No result in decision block 680), identical to the test performed in decision block 360. If the duration of the local peak maximum does not exceed THamp for at least the duration of THwin, the signal envelope is evaluated in decision block 670, as before, to determine if there is another local maximum. If no further envelope peaks are detected (a No result in decision block 670) then it is determined that there is no first arrival packed detected (block 699) in the signal envelope, and the detection process for the selected path is completed. If, however, a local maximum peak exceeds THamp for at least the duration of THwin (a Yes result in decision blocks 660 or 680) that pulse segment is determined to be a first arrival pulse (block 695). In that case t1, the pulse arrival time, as described above, is the time at which that pulse segment first exceeds THamp. In no case may t1 be less than $T_1^k$. The detection process may then be repeated for another path.

This decision methodology may be found beneficial where the pulse signals detected are good quality (i.e., having only one or a few local maxima), clearly separable from both cross-talk and scattered pulse signals, are of sufficient amplitude to set a reasonable threshold. Because the signal processing requirements may be considerable, this decision methodology may be beneficial where the number of paths in array 110 may be less than a selected maximum number dependent on the processing capability and speed of the structural health monitoring system.

It may now be appreciated that the choice of THwin may be selected to substantially improve reliability of detection by requiring the first arrival pulse width to be greater than THwin. As indicated above, THwin bears a corresponding relation to the exciting pulse width at the transmitting sensor and the resonant response of the sensor to the excitation. Thus, THwin is selected with the expectation that the received signal is greater than THamp for at least the duration of THwin. A narrower pulse may imply damage directly in the path of the transmitted wave, which attenuates the pulse, consequently reducing the pulse width that exceeds THamp, or there may be sensor damage, in which case data obtained from that sensor (as a transmitter or detector) is considered unreliable. The size of THwin, together with THamp, thus determines whether a pulse with a local maximum is wide and strong enough to qualify as a pulse representing the first arrival.

It may further be appreciated that varying THamp and THwin will result in different degrees of accurately determining the first arrival. Increasing THamp will reduce the likelihood of detecting any signal of marginal amplitude, whereas lowering THamp may increase the detection of noise that may be mistaken for a possible first maximum. The beginning of THwin, i.e., t1, must be at least greater than $T_1^k$, the lower bound on transmission time for the kth path.

In a similar manner, the arrival of reflection pulse signals may be determined by assigning a time t1' that begins after the end of the time window THwin for the first arrival signal, a threshold amplitude value for reflection signals may be defined, and the same search procedure applied.

Appendix C

A reasoning process may be used to check for degraded transducers. This reasoning process involves comparing signals on paths going directly through a suspect transducer 210 to signals obtained from prior baseline measurements. If there are signal differences between the obtained data and baseline data for all actuator-sensor paths associated with a given PZT transducer, but there are no substantial signal changes on paths going directly through a particular transducer in question to a third transducer directly in line with the first two, then this is an indication of a degraded transducer (for example, partially damaged or disbanded).

For example, referring to FIG. 7, assuming that all transducers 210 under consideration satisfy impedance measurement criteria for acceptable performance, if paths 1→2 and 2→3 between transducers #1 and #2 and between #2 and #3 show signal changes, including either a weakened signal or loss of signal, but path 1→3 between transducers 1 and 3 does not show any changes relative to baseline data records, then this may indicate transducer #2 may be partially damaged or completely disbanded. Similarly, if path 1→2 shows no change, but 1→3 and 2→3 show changes, then this indicates that transducer #3 is suspected of degradation. Because the configuration is symmetric about transducer #2, #1 may be similarly diagnosed. Alternative combinations, in which the path direction is reversed, may be considered, and reciprocity predicts that the observed results will be the same. Thus, if array 215 has at least three transducers 210 arranged sequentially in line with each other, and one of the transducers may be defective, it can be identified, whether it is an interior transducer 210 of array 215 or an edge transducer 210 of array 215.

Given this ability to detect disbanded transducers, which may impact the capacity of an array 215 with a designated set of pitch-catch paths to detect structural defects of a given minimum size, the next step in self-diagnostics involves strategies for "self-healing" array 215 to retain the full coverage of the structure. Self-healing is an adaptive process, for example, of adding new pitch-catch paths between different pairs of transducers than were previously selected in order to cover the same area as previously provided, or to guarantee that the new paths provide coverage that enables detection of defects having greater than a specified minimum size within the array area.

FIG. 8 illustrates, as an exemplary case, how new-path generation can be implemented to maintain coverage in a 3×3 array 815 of transducers 810 for detecting defect 820, the size of which may be characterized by a circle of at least a specified minimum diameter. Coverage may be considered sufficient, for example, when paths can be generated to detect defects equal or greater than a selected size. Thus, when new paths are generated to satisfy coverage sufficiency, the test may be whether any defect of at least a selected size is detectable with the new set of paths. A defect of at least a selected size may be considered detectable if it always intersects at least one pitch-catch path when located anywhere within the transducer array. Other criteria defining coverage may be selected, the above description being only exemplary, and is not intended to be limiting. For example, selected criteria may be dependent on the length of the new path as well as on the amplitude and/or time-of-arrival of pulse signals.

FIG. 8A represents array 815 with, for example, a generally square array of 9 transducers 810 in a 3×3 matrix. Defect 820 may be located in the top left quadrant of array 815. Paths between all adjacent vertical, horizontal or diagonal transducers 810 are indicated by broken double arrow lines. Defect 820 is clearly intersected, for example, by a path connecting the top left-most and center transducers 810.

FIG. 8B represents array 815 when center transducer 810 of array 815 is found, as a result of self-diagnosis method 400, missing, disbanded, or otherwise inoperative for structural health monitoring. All paths associated with defective (or missing) center transducer 810 are removed from the array (for purposes of data collection). Defect 820 now occupies a region of the structure not covered by any of the remaining pitch-catch paths specified in the original configuration. Since coverage may now be insufficient to detect a defect 820 of at least the specified size, paths between other transducer pairs 810 may be added or extended to pass through the location of the missing transducer 810 or otherwise guarantee that defect 820 will be intersected by a path between two remaining transducers 810.

FIG. 8C represents array 815 with new paths added: diagonal paths between transducers 810 at opposite corners and horizontal and vertical paths between transducers 810 at the mid-points of the edges of array 815. Thus, in effect, all pitch-catch trajectories are recovered, and defect 820 now lies in at least one of the added paths, and may be detected. Accordingly, to verify self-diagnosis healing with pitch-catch signal transmission along the selected paths to determine if disbond defects still exist. When the predicted coverage is then obtained, testing of pitch-catch signals along the defined paths may be tested.

FIG. 9 illustrates an example of loss of a transducer 910 at a corner of an array 915, where the benefit of simply extending a path is not available. FIG. 9A is substantially identical to FIG. 8A. Defect 920 is located in substantially the same place and is of substantially the same size as defect 820. In FIG. 9B, the loss of the top left-most transducer results in the removal of three paths—one of which intersects defect 820 on a diagonal path with center transducer 910 of array 915. Method 600 may then add a new "alternate" diagonal path D that may intersect defects such as defect 920 located at the same position.

In cases where more than one transducer may be disbanded, where arrays of such transducers are typically arranged at least in two dimensions and/or consist of more than three transducers arranged in-line (i.e., collinearly), equivalent test scenarios may be implemented to verify each transducer for a disbond by using more complex (e.g., next-nearest neighbor in-line) paths.

Therefore, as illustrated in the above cases, testing path transmission between transducers and comparison to baseline data may enable detection of damaged or disbanded transducers 810 that are not apparent from simple pass/fail impedance measurements alone.

What is claimed is:

1. A method of improving damage detection in a structural health monitoring system, comprising:
    obtaining a baseline set of signals corresponding to a range of values of an environmental effect variable for a plurality of first selected paths between pairs of a plurality of sensors configured in an array attached to a structure;
    establishing threshold levels for each of the first selected paths for determining detection of damage in the structure based on differences among the signals in the baseline set of signals for the selected path;
acquiring, from the plurality of sensors attached to the structure, a current signal for each of the selected paths;
in a digital computer, analyzing the current signals based on the threshold levels to detect damage in the structure, wherein the analyzing further comprises:
for each of the selected paths, determining at least one first arrival index value according to a difference between a first arrival portion of the corresponding current signal and one of the corresponding baseline signals;
determining second selected paths that have a first arrival index value exceeding the corresponding threshold level; and
detecting the damage according to at least one of a number of the second selected paths that are adjacent to each other, and a number of the second selected paths that cross each other.

2. The method of claim 1, wherein obtaining the baseline set comprises self-diagnosing the integrity of the one or more sensors, wherein the self-diagnosing comprises:
measuring impedances of the one or more sensors;
comparing the impedances to reference values; and
determining that the sensor is accepted or rejected on the basis of the comparing.

3. The method of claim 2, wherein the self-diagnosing further comprises:
transmitting a signal from a first accepted sensor to a second and a third accepted transducer, wherein the first, second and third accepted sensors are arranged in an inline sequential configuration;
detecting the signal at the second and third accepted sensors;
comparing the detected transmitted signals to selected reference signal criteria, the selected reference signal criteria being based on transducers known to be properly functioning and properly bonded to a baseline structure; and
determining from the compared detected signals if any of the sensors of the one or more pairs of the sensors is bonded, or completely or partially disbonded.

4. The method of claim 3, wherein the self-diagnosing further comprises:
determining whether pairs of the plurality of sensors provide one or more alternate second paths that traverse at least a portion of the paths of the first selected paths associated with rejected transducers or completely or partially disbonded sensors;
selecting the alternate second paths to replace the first selected paths; and
obtaining baseline signals from the accepted first selected paths and the alternate second paths.

5. The method of claim 1, wherein the each of the baseline signals for the selected paths has a first arrival portion.

6. The method of claim 5, wherein the obtaining a baseline set of signals comprises selecting one baseline signal corresponding to a selected value of an environmental effect as a reference baseline signal.

7. The method of claim 6, wherein establishing the threshold comprises:
defining the first arrival index corresponding to differences between the reference baseline signal and the remaining baseline signals for the associated selected path, the one or more baseline signals corresponding to different values of the environmental variable.

8. The method of claim 7, wherein the difference is based on time of arrival of the first arrival signal.

9. The method of claim 7, wherein the difference is based on a Euclidean distance calculation of digitized first arrival portions of the reference and the remaining baseline signals.

10. The method of claim 7, wherein a first arrival index threshold is selected on the basis of the difference between the selected reference baseline signal and one of the remaining baseline signals.

11. The method of claim 10, wherein the analyzing further comprises:
determining if the first arrival index of the current signal for a selected path exceeds the first arrival index threshold, wherein no damage is found if the first arrival index does not exceed the first arrival index threshold.

12. The method of claim 7, wherein the current signal has a first arrival portion.

13. The method of claim 12, wherein the analyzing the current signal comprises:
matching the first arrival portion of the current signal for the selected path to the best match of the baseline signals, wherein the best match is determined according to the baseline signal having the smallest difference from the current signal; and
defining a first arrival index corresponding to the current signal based on the smallest difference.

14. The method of claim 13, wherein the smallest difference is determined by a minimum difference in time of arrival between the first arrival portion of the current signal and one of the baseline signals, or by a minimum Euclidean distance calculation between the first arrival portion of the current signal and the first arrival portion of the one of the baseline signals.

15. The method of claim 7, wherein the current signal has a reflection portion.

16. The method of claim 15, further comprising:
time shifting the reflection portion to overlap with the first arrival portion of the baseline signal that is the best fit to the first arrival portion of the current signal.

17. The method of claim 16, further comprising:
defining a reflection index corresponding to the difference between the time shifted reflection portion of the current signal and the best fit baseline signal.

18. The method of claim 17, further comprising selecting a threshold value of the reflection index.

19. The method of claim 18, wherein the detecting further comprises:
determining, when the first arrival index of the current data signal for a selected path exceeds the first arrival index threshold, if the first arrival index of the current data signal for an adjacent path exceeds the first arrival index threshold; and
determining, when the first arrival index of the current data for a selected path exceeds the first arrival index threshold, if the first arrival index of the current data signal for a one or more other paths crossing the selected path exceed the first arrival index threshold.

20. The method of claim 19, wherein the detecting further comprises:
determining, when there are more than two current data signal first arrival indices in other crossing paths that exceed the first arrival index threshold, that damage exists;
determining an upper bound for a size of the damage; and
calculating the probability of detection for the damage size.

21. The method of claim 19, wherein the detecting further comprises:

determining, when there are only two other crossing paths, if there are one or more paths adjacent to the selected path having a reflection index of the current data signal that exceeds the selected reflection index threshold.

22. The method of claim 21, wherein the detecting further comprises:
   determining, if there is no adjacent path having an associated reflection index exceeding the reflection index threshold, that no damage is detected.

23. The method of claim 21, wherein the detecting further comprises:
   determining, if there is one or more adjacent paths having an associated reflection index exceeding the reflection index threshold, that damage is detected;
   determining an upper bound for damage size on the basis of the current data signals of the selected and adjacent paths; and
   calculating the probability of detection for corresponding damage size.

24. The method of claim 19, wherein the detecting further comprises:
   determining, when the first arrival index of the current signal for an adjacent path exceeds the first arrival index threshold, if there are two or more adjacent paths having current signal reflection indices that exceed the first arrival threshold.

25. The method of claim 24, wherein the detecting further comprises:
   determining, if there are not two or more adjacent paths having current signal reflection indices that exceed the reflection index threshold, that no damage is detected for the selected path.

26. The method of claim 24, wherein the detecting further comprises:
   determining, if there are two or more adjacent paths having current data signal reflection portions that exceed the threshold, that damage is detected for the selected path;
   determining the upper bound for damage size on the basis of the current data signals of the selected and adjacent paths; and
   calculating the probability of detection for corresponding damage size.

* * * * *